United States Patent
Tajima

(10) Patent No.: US 8,971,494 B2
(45) Date of Patent: Mar. 3, 2015

(54) RADIATION IMAGING APPARATUS AND CONTROL METHOD THEREOF, AND RADIATION IMAGING SYSTEM

(71) Applicant: FUJIFILM Corporation, Tokyo (JP)

(72) Inventor: Takashi Tajima, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 293 days.

(21) Appl. No.: 13/676,255

(22) Filed: Nov. 14, 2012

(65) Prior Publication Data

US 2013/0121464 A1 May 16, 2013

(30) Foreign Application Priority Data

Nov. 15, 2011 (JP) .................................. 2011-249591

(51) Int. Cl.
*H05G 1/56* (2006.01)
*A61B 6/00* (2006.01)

(52) U.S. Cl.
CPC ............... *A61B 6/542* (2013.01); *A61B 6/4233* (2013.01); *A61B 6/4283* (2013.01); *A61B 6/548* (2013.01)
USPC ................ 378/97; 378/96; 378/108; 385/132

(58) Field of Classification Search
USPC .......... 378/62, 87, 91, 96–98, 98.7, 108–112, 378/117, 165; 382/132, 270, 325
See application file for complete search history.

(56) References Cited

U.S. PATENT DOCUMENTS

| 7,639,779 | B2 | 12/2009 | Kashiwagi et al. | |
|---|---|---|---|---|
| 2006/0013465 | A1* | 1/2006 | Nonaka | 382/132 |
| 2013/0077744 | A1* | 3/2013 | Kamiya | 378/62 |
| 2013/0148782 | A1* | 6/2013 | Tajima | 378/62 |
| 2013/0202086 | A1* | 8/2013 | Tsuji | 378/62 |
| 2013/0208860 | A1* | 8/2013 | Sugizaki | 378/62 |
| 2013/0223592 | A1* | 8/2013 | Sato | 378/62 |
| 2013/0251106 | A1* | 9/2013 | Tajima | 378/62 |
| 2014/0177798 | A1* | 6/2014 | Kitagawa et al. | 378/62 |
| 2014/0205066 | A1* | 7/2014 | Kitagawa et al. | 378/62 |

FOREIGN PATENT DOCUMENTS

JP 2007-236804 A 9/2007

* cited by examiner

*Primary Examiner* — Bernard E Souw
(74) *Attorney, Agent, or Firm* — Birch, Stewart, Kolasch & Birch, LLP

(57) ABSTRACT

Besides normal pixels, a plurality detection pixels are arranged in an imaging surface of an FPD. In preliminary imaging, X-rays are emitted to an imaged body portion of a patient. The detection pixels receive the X-rays passed through the body portion, and output AEC detection signals. If an integral value of the AEC detection signals has reached a threshold value, X-ray emission is stopped and the preliminary imaging is completed. A main exposure condition determination unit determines a main irradiation time, being an irradiation time with the X-rays during the main imaging, based on an irradiation time with the X-rays during the preliminary imaging and the integral value of the AEC detection signals. The main imaging is performed using the main irradiation time. The normal pixels continue a charge accumulation operation over the preliminary imaging and the main imaging to produce an X-ray image for use in diagnosis.

15 Claims, 10 Drawing Sheets

| IMAGED PORTION | TUBE VOLTAGE (kV) | TUBE CURRENT (mA) | IRRADIATION AREA | THRESHOLD VALUE | NECESSARY X-RAY DOSE |
|---|---|---|---|---|---|
| ⋮ | ⋮ | ⋮ | ⋮ | ⋮ | ⋮ |
| CHEST AP | V1 | I1 | | TH1 | X1 |
| CHEST PA | V2 | I2 | | TH2 | X2 |
| ⋮ | ⋮ | ⋮ | ⋮ | ⋮ | ⋮ |

RADIATION IMAGING APPARATUS AND CONTROL METHOD THEREOF, AND RADIATION IMAGING SYSTEM

BACKGROUND OF THE INVENTION

1. Field of the Invention

The present invention relates to a radiation imaging apparatus that performs preliminary imaging and main imaging in sequence, a control method of the radiation imaging apparatus, and a radiation imaging system.

2. Description Related to the Prior Art

In a medical field, a radiation imaging system, for example, an X-ray imaging system using X-rays is widely known. The X-ray imaging system is constituted of an X-ray generating apparatus for generating the X-rays, and an X-ray imaging apparatus for taking an X-ray image by reception of the X-rays. The X-ray generating apparatus includes an X-ray source for emitting the X-rays to a patient's body, a source controller for controlling the operation of the X-ray source, and an emission switch for issuing an emission start command of the X-rays. The X-ray imaging apparatus includes an X-ray image detecting device for detecting the X-ray image based on the X-rays passed through the patient's body, and a console for controlling the operation of the X-ray image detecting device and applying various image processes to the X-ray image.

In recent years, the X-ray image detecting device that uses a flat panel detector (FPD) instead of an X-ray film or an imaging plate (IP) becomes widespread. The FPD has a matrix of pixels each of which produces signal charge by an amount corresponding to the amount of the X-rays incident thereon and accumulates the signal charge therein. The FPD accumulates the signal charge on a pixel-by-pixel basis, and converts the accumulated signal charge into a voltage signal by its signal processing circuit. Thereby, the FPD electrically detects the X-ray image, and outputs the X-ray image as digital image data.

An electronic cassette (portable X-ray image detecting device) that has the FPD contained in a flat slim housing is in practical use. The electronic cassette is mounted not only on a specific imaging stand, but also on an existing imaging stand shareable between a film cassette and an IP cassette. Furthermore, the electronic cassette is sometimes used while being put on a bed or held by the patient himself/herself. The electronic cassette is sometimes brought out from a hospital for use in bedside radiography of a home-care patient or in an outside accident or natural disaster site in an emergency.

The X-ray image detecting device having an automatic exposure control (AEC) function is widely known. In such a device, the FPD is provided with a dose detection sensor for detecting an X-ray dose. If an integral value of the X-ray dose detected by the dose detection sensor reaches a predetermined threshold value, an emission stop signal is transmitted to the X-ray source to stop generation of the X-rays.

In the AEC, if the source controller delays performing X-ray stop operation, the image quality of the X-ray image is degraded and moreover the patient is exposed to an unnecessary dose. For example, in mammography, the time between the start of X-ray emission and the stop thereof is extremely short, of the order of 50 ms, and hence it is required to perform the X-ray stop operation as quick as possible immediately after application of a sufficient X-ray dose is ensured. However, in actual fact, the transmission delay and propagation delay between the source controller and the X-ray image detecting device tends to retard the X-ray stop operation.

Therefore, as a method for reliably performing the X-ray stop operation without using the AEC at the timing that the desirable X-ray image is obtainable, a technique is proposed in which preliminary imaging is performed before main imaging, and an X-ray dose in the main imaging is controlled based on a result of the preliminary imaging. For example, in a radiation image capturing apparatus of U.S. Pat. No. 7,639,779, a radiation dose necessary for the preliminary imaging is calculated based on measured thickness of a breast and pressing pressure on the breast. Then, a radiation dose necessary for the main imaging is calculated based on an actual radiation dose detected during the preliminary imaging by a dose detection sensor. In each of the preliminary imaging and the main imaging, a tube current of an X-ray source is controlled in accordance with the calculated radiation dose. Japanese Patent Laid-Open Publication No. 2007-236804 discloses measuring pressing pressure on a breast being pressed by a board, determining a radiation dose for the preliminary imaging that is less than that for the main imaging in accordance with the pressing pressure, calculating an index value (the sum of pixel values of a breast area) by performing the preliminary imaging, and determining an exposure condition (current-time product) of the main imaging based on the difference between the index value and a predetermined reference value and a table representing the relation between the difference and a time-current product.

However, the U.S. Pat. No. 7,639,779 takes time and effort to measure the thickness of the breast and the pressing pressure on the breast, for the purpose of determining the radiation dose for the preliminary imaging. Likewise, the Japanese Patent Laid-Open Publication No. 2007-236804 also needs time and effort to measure the thickness of the breast and calculate the radiation dose for the preliminary imaging based on the measured thickness and to calculate the index value by analysis of an image obtained in the preliminary imaging.

SUMMARY OF THE INVENTION

An object of the present invention is to provide a radiation imaging apparatus that can always perform radiography with an optimal radiation dose with minimum time and effort, a control method of the radiation imaging apparatus, and a radiation imaging system having the radiation imaging apparatus.

To achieve the above and other objects, a radiation imaging apparatus according to the present invention includes a radiation image detecting device, a dose detection sensor, an automatic exposure controller, and a main exposure condition determination unit. The radiation image detecting device has a detection panel having an arrangement of a plurality of pixels each for receiving radiation emitted from a radiation source and passed through an imaged portion. The dose detection sensor detects a received radiation dose passed through the imaged portion. The automatic exposure controller compares an integral value of the received radiation dose with a predetermined threshold value, and automatically stops emission of the radiation from the radiation source in preliminary imaging if the integral value has reached the threshold value. The main exposure condition determination unit determines a main exposure condition based on the integral value of the received radiation dose detected during the preliminary imaging and a necessary radiation dose required for ensuring image quality of a radiographic image. The main exposure condition includes a main irradiation time being an irradiation time with the radiation during main imaging or a main time-current product being a time-current product used during the main imaging. The main imaging is carried out with use of the determined main exposure condition.

The dose detection sensor is preferably provided in the detection panel.

It is preferable that the radiation imaging apparatus further includes a timer for measuring a preliminary irradiation time, being an irradiation time with the radiation during the preliminary imaging. The main exposure condition determination unit determines the main exposure condition in consideration of the preliminary irradiation time measured by the timer, in addition to the integral value of the received radiation dose and the necessary radiation dose.

The main exposure condition determination unit may divide the integral value of the received radiation dose during the preliminary imaging by the preliminary irradiation time or the current-time product during the preliminary imaging, to calculate the received radiation dose per unit of time or per unit of the current-time product. The integral value of the received radiation dose may be subtracted from the necessary radiation dose, and a subtraction result may be divided by the received radiation dose per unit of time or per unit of the current-time product to calculate the main irradiation time as the main exposure condition.

The radiation image detecting device is preferably shifted to the main imaging without discharging electric charge that is produced and accumulated in the pixels during the preliminary imaging. After completion of the main imaging, the radiographic image is produced from the electric charge accumulated in the pixels over the preliminary imaging and the main imaging.

A plurality of dose detection sensors may be uniformly or locally distributed in an imaging surface of the detection panel. The radiation imaging apparatus may further include a detection sensor selector for selecting at least one of the dose detection sensors in accordance with the imaged portion. The automatic exposure control and determination of the main exposure condition may be performed with use of a detection result from the selected dose detection sensor.

The plurality of pixels may include a normal pixel for producing and accumulating signal charge in accordance with a radiation dose received therein and outputting the signal charge through a switching element to a signal line, and a detection pixel connected directly to the signal line. Otherwise, the plurality of pixels may include the normal pixel and another detection pixel having a switching element driven independently of the switching element of the normal pixel. The detection pixel functions as the dose detection sensor.

The radiation image detecting device may be an electronic cassette having the detection panel contained in a portable housing.

A control method of the radiation imaging apparatus according to the present invention includes the steps of emitting radiation from the radiation source to the imaged portion in preliminary imaging; detecting the radiation dose received in a radiation image detecting device through the imaged portion; comparing the integral value of the received radiation dose with the predetermined threshold value; automatically stopping emission of the radiation from the radiation source and completing the preliminary imaging, if the integral value has reached the threshold value; determining the main exposure condition based on the integral value of the received radiation dose detected during the preliminary imaging and the necessary radiation dose required for ensuring the image quality of the radiographic image; and carrying out the main imaging with use of the determined main exposure condition.

The control method further includes the step of measuring the preliminary irradiation time being the irradiation time with the radiation during the preliminary imaging. In the step of determining the main exposure condition, the main exposure condition is preferably determined in consideration of the preliminary irradiation time, in addition to the integral value of the received radiation dose and the necessary radiation dose.

A radiation imaging system according to the present invention includes a radiation generating apparatus for emitting radiation to the imaged portion and the radiation imaging apparatus described above.

According to the present invention, the automatic exposure control is performed in the preliminary imaging. The main imaging is carried out with the main irradiation time or the current-time product that is determined based on a result of the preliminary imaging. Thus, the present invention eliminates the need for measuring the thickness of a breast for the preliminary imaging, calculating a radiation dose, calculating an index value based on image data obtained in the preliminary imaging, and the like. Therefore, it is possible to carry out the main imaging easily with an appropriate radiation dose.

BRIEF DESCRIPTION OF THE DRAWINGS

For more complete understanding of the present invention, and the advantage thereof, reference is now made to the subsequent descriptions taken in conjunction with the accompanying drawings, in which.

DESCRIPTION OF THE PREFERRED EMBODIMENTS

Figure 1:
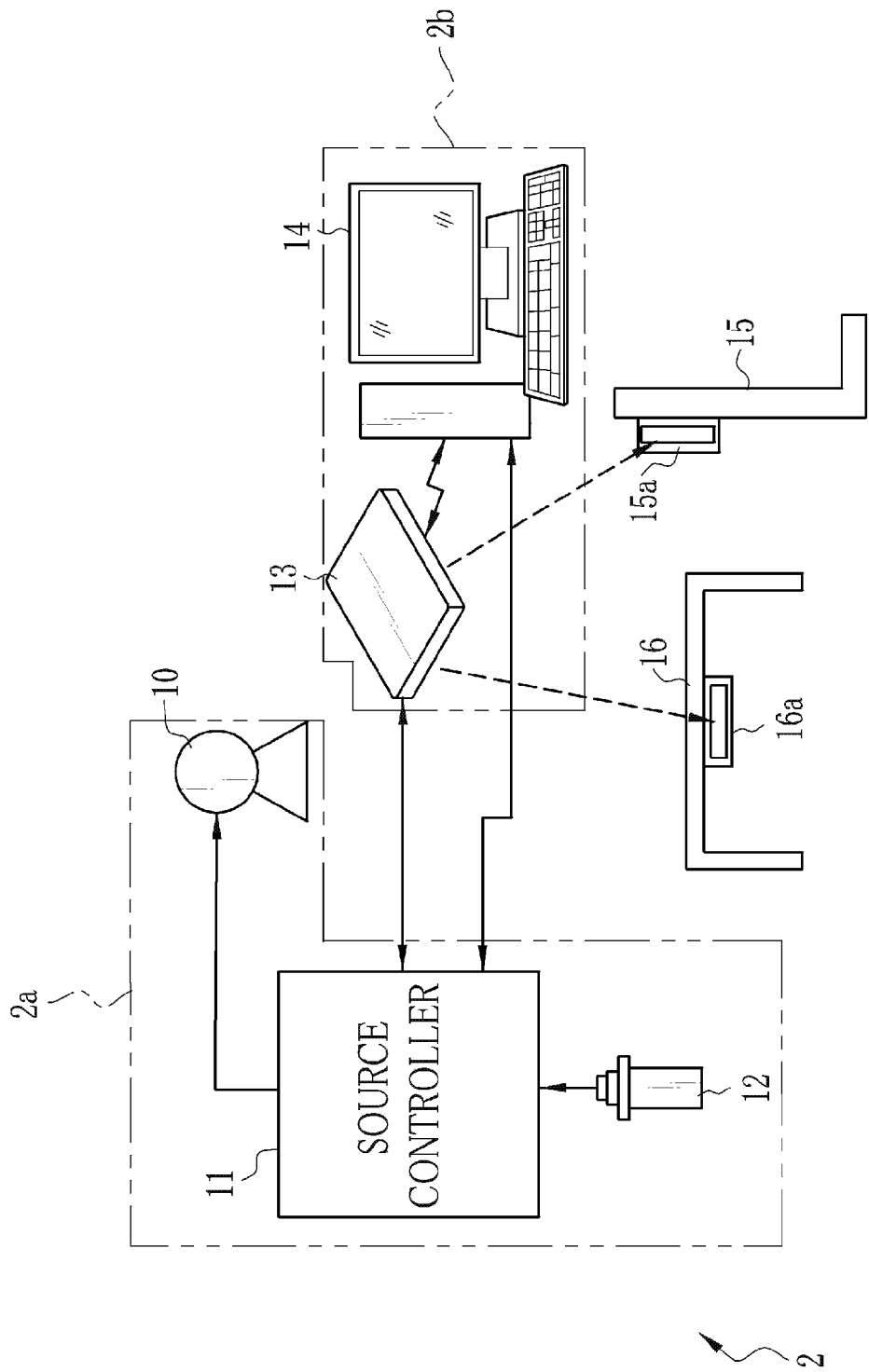
FIG. 1 is a schematic view of an X-ray imaging system.

As shown in FIG. 1, an X-ray imaging system 2 is constituted of an X-ray source 10, a source controller 11, an emission switch 12, an electronic cassette 13, a console 14, and an imaging stand 15, and an imaging table 16. The X-ray source 10 contains an X-ray tube for emitting X-rays. The source controller 11 controls the operation of the X-ray source 10. The emission switch 12 commands the start of X-ray emission. The electronic cassette 13 detects the X-rays that have passed through an object e.g. a patient's body to output an X-ray image. The console 14 controls the operation of the electronic cassette 13, and performs image processing on the X-ray image. The imaging stand 15 and the imaging table 16 are used in performing radiography of the patient in a standing position and a lying position, respectively. In addition to above, the X-ray imaging system 2 has a source shift mechanism (not shown) for setting the X-ray source 10 in a desired orientation and position. Reference numerals 15a and 16a refer to a holder into which the electronic cassette 13 is loaded.

The X-ray imaging system 2 performs preliminary imaging and main imaging to obtain an X-ray image of the object. In the preliminary imaging, an X-ray dose less than that of the main imaging is applied to an imaged portion of the object in order to determine an exposure condition used in the main imaging (hereinafter called main exposure condition). The main imaging is performed with the determined main exposure condition to obtain the X-ray image for use in diagnosis.

The X-ray source 10 has an X-ray tube for emitting the X-rays, and a collimator for limiting an irradiation field of the X-rays. The X-ray tube has a cathode being a filament for emitting thermoelectrons, and an anode (target) for radiating the X-rays by collision of the thermoelectrons emitted from the cathode. The collimator is composed of, for example, four X-ray shielding lead plates disposed on each side of a rectangle so as to form an irradiation opening in its middle through which the X-rays propagate. Changing the positions of the lead plates can vary the size of the irradiation opening to determine the irradiation field.

Figure 2:
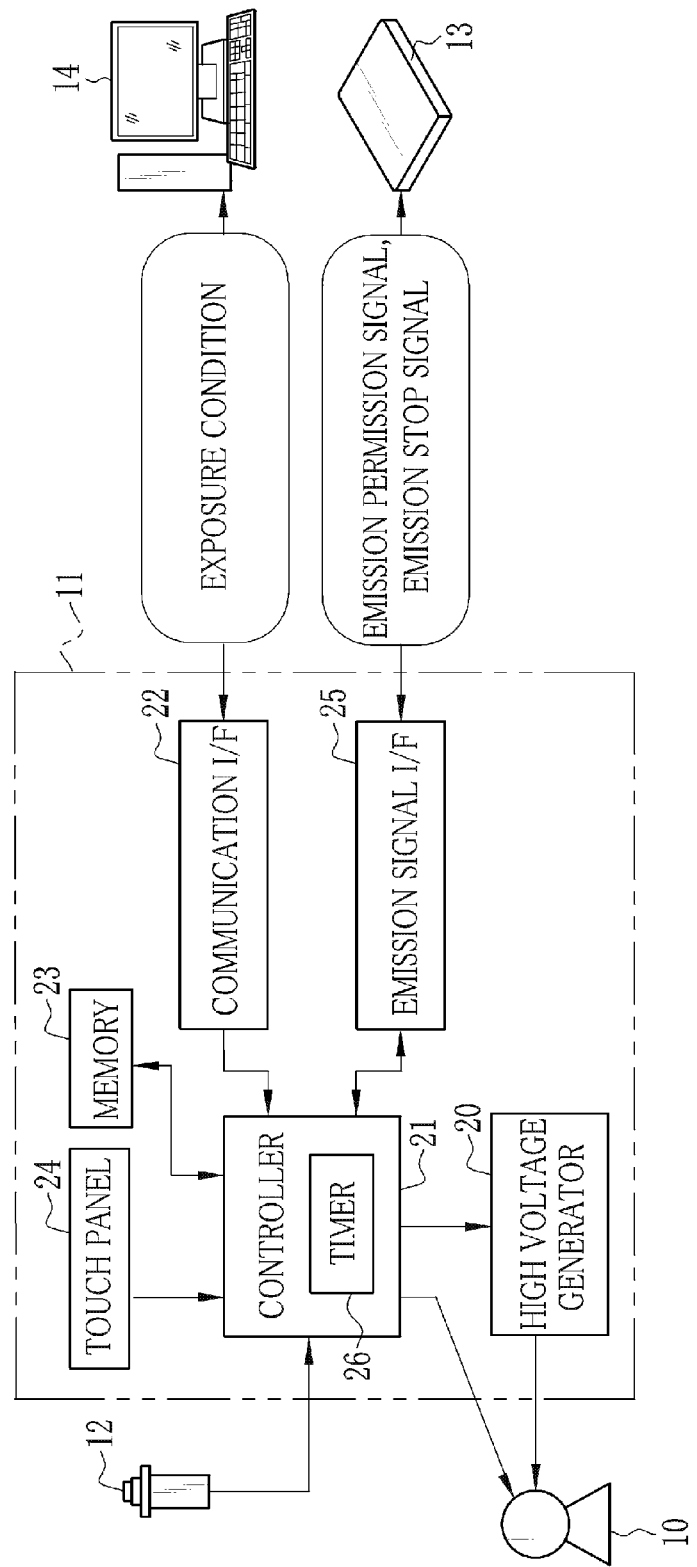
FIG. 2 is a block diagram showing the structure of a source controller and the connection between the source controller and other devices.

As shown in FIG. 2, the source controller 11 includes a high voltage generator 20, a controller 21, and a communication I/F 22. The high voltage generator 20 produces a high voltage by multiplying an input voltage using a transformer, and supplies the high voltage to the X-ray source 10 as a tube voltage through a high voltage cable. The controller 21 controls the tube voltage for determining an energy spectrum of the X-rays, a tube current for determining an X-ray irradiation amount per unit of time, and an X-ray irradiation time. The communication I/F 22 mediates transmission and reception of essential information and signals between the source controller 11 and the console 14.

To the controller 21, the emission switch 12, a memory 23, and a touch panel 24 are connected. The emission switch 12 is a two-step press switch operated by a radiological technician. Upon a half press of the emission switch 12, a warm-up start signal is issued to start warming up the X-ray source 10. Upon a full press of the emission switch 12, an emission start signal is issued to start emitting the X-rays from the X-ray source 10. These signals are inputted to the source controller 11 through a signal cable. The controller 21 starts supplying electric power from the high voltage generator 20 to the X-ray source 10 in response to the emission start signal from the emission switch 12, to perform the preliminary imaging and the main imaging in sequence.

Several types of exposure conditions each including the tube voltage, the tube current, and the like are stored in advance in the memory 23. The radiological technician manually chooses an appropriate exposure condition out of the several types of exposure conditions through the touch panel 24. The tube voltage and the tube current take the same values in both the preliminary imaging and the main imaging. In the preliminary imaging, a planned irradiation time is set at its maximum value so as to prevent a situation in which the X-ray emission is completed before an AEC circuit 67 (see FIGS. 4 and 6) of the electronic cassette 13 commands the stop of X-ray emission and a received X-ray dose becomes insufficient. On the other hand, in the main imaging, the irradiation time is set at a value that is determined based on the preliminary imaging. In the preliminary imaging, the source controller 11 starts the X-ray emission with the set tube voltage, tube current, and planned irradiation time (maximum value). At the instant when the AEC circuit 67 detects that the received X-ray dose has reached a dose value required for determining the main exposure condition, the AEC circuit 67 stops the X-ray emission even if measured irradiation time has not yet reached the planned irradiation time. The planned irradiation time (maximum value) set in the preliminary imaging is preferably changed in accordance with the imaged body portion.

Figure 3:
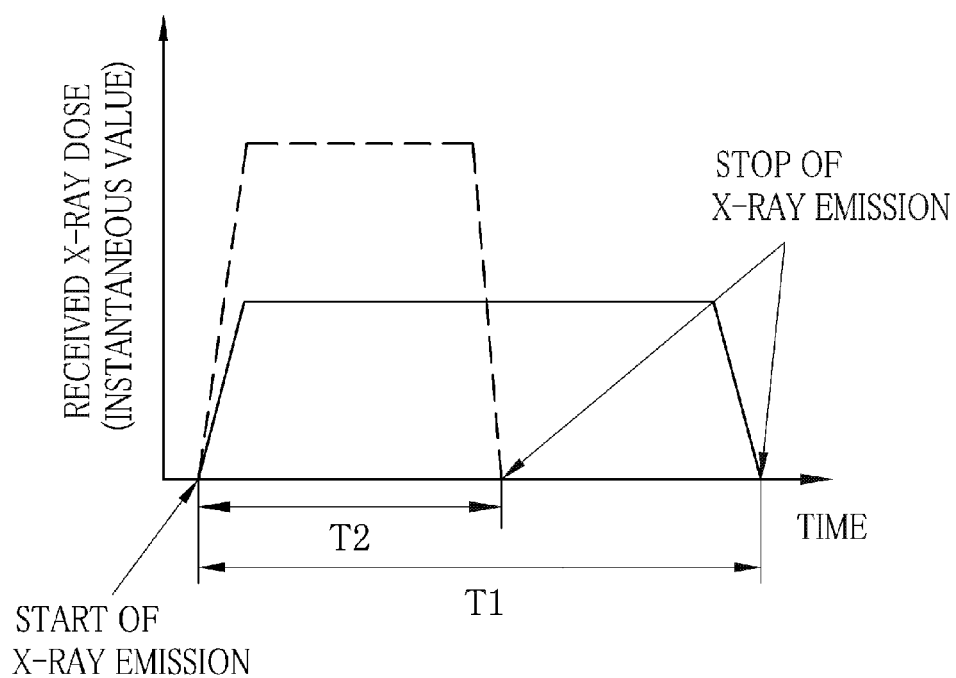
FIG. 3 is a graph showing the relation between an instantaneous value of a received X-ray dose and time in preliminary imaging.

Since the X-ray dose necessary to the preliminary imaging is much less than that necessary to the main imaging, the X-ray emission in the preliminary imaging is stopped before the planned irradiation time in actual fact, though the planned irradiation time is set at its maximum value in the source controller 11. In FIG. 3, in the case of emitting the X-rays with the same tube voltage and the same tube current, if the thickness of the patient's body is relatively large, as shown by a solid line, an instantaneous value of an X-ray dose that is received per unit of time by an imaging surface 36 of an FPD 35 (see FIG. 4) through the body becomes small, so an irradiation time T1 to achieve a necessary X-ray dose becomes long. On the other hand, if the thickness of the patient's body is relatively small, as shown by a broken line, an irradiation time T2 becomes short. Similarly, if the density of internal body tissue is relatively high, an irradiation time becomes long due to reduction in X-ray transmittance. If the density of the internal body tissue is relatively low, an irradiation time becomes short. Although the irradiation time varies in accordance with the body thickness and the density of the internal body tissue, as described above, an integral value (the size of a trapezoidal area) of the received X-ray dose is always constant and equal to the necessary X-ray dose.

An emission signal I/F 25 connected to the electronic cassette 13 transmits and receives signals between the electronic cassette 13 and the controller 21. Upon receiving the warm-up start signal from the emission switch 12, the controller 21 transmits an inquiry signal to the electronic cassette 13 through the emission signal I/F 25. In response to the inquiry signal, the electronic cassette 13 completes a reset operation and prepares for a charge accumulation operation. Then, if the source controller 11 receives from the electronic cassette 13 an emission permission signal being a response to the inquiry signal at the emission signal I/F 25 and the emission start signal from the emission switch 12, the controller 21 starts supplying the electric power from the high voltage generator 20 to the X-ray source 10. If the source controller 11 receives an emission stop signal from the electronic cassette 13 at the emission signal I/F 25, the controller 21 stops supplying the electric power from the high voltage generator 20 to the X-ray source 10, to stop the X-ray emission. As described above, the controller 21 controls the stop timing of the X-ray emission based on the signal from the electronic cassette 13 in the preliminary imaging. In addition, the controller 21 measures a duration of the X-ray emission by a timer 26 contained therein, and stops the X-ray emission if the measured duration has reached the set irradiation time.

Figure 4:
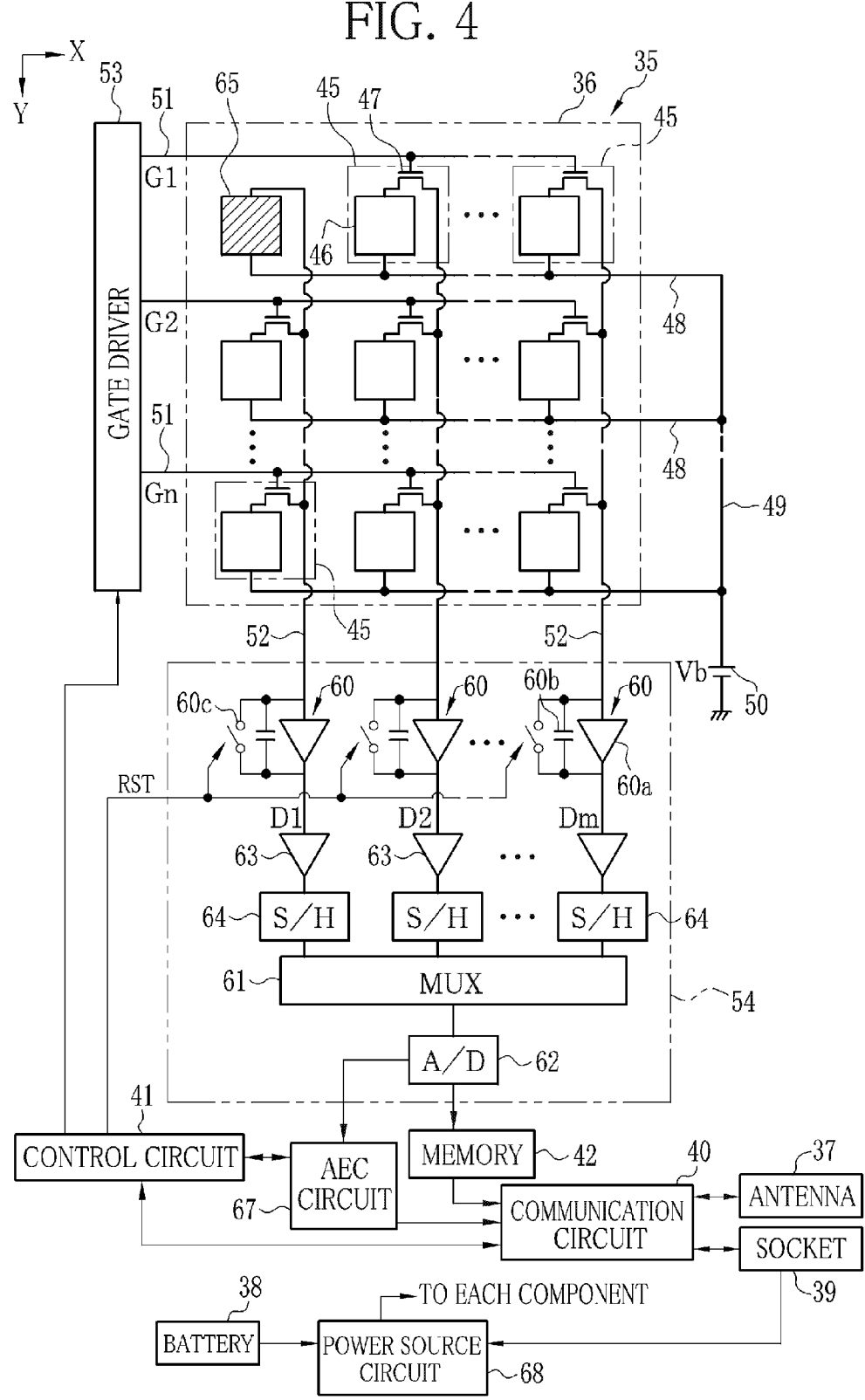
FIG. 4 is a block diagram of an electronic cassette.

In FIG. 4, as is widely known, the electronic cassette 13 is composed of the FPD 35 and a portable housing (not shown). The housing of the electronic cassette 13 is in a rectangular flat box shape and approximately the same size as those of a film cassette and an IP cassette (also called CR cassette), in other words, is compatible with International Standard ISO4090:2001 in size and shape. Thus, the electronic cassette 13 is mountable on an existing imaging stand or table shareable between the film cassette and the IP cassette.

The electronic cassette 13 is detachably mounted on the holder 15a or 16a (see FIG. 1) of the imaging stand 15 or the imaging table 16 in such a position that the imaging surface 36 of the FPD 35 is opposed to the X-ray source 10. There are both the imaging stand 15 and the imaging table 16 installed in an examination room, so a plurality of electronic cassettes are generally provided in the examination room. The electronic cassette 13 is sometimes used separately from the imaging stand 15 or the imaging table 16 in a state of being put on a bed under the patient's body or held by the patient himself/herself.

The electronic cassette 13 that contains an antenna 37 and a battery 38 can establish wireless communication with the console 14. The antenna 37 transmits and receives a radio wave for use in the wireless communication to and from the console 14. The battery 38 supplies electric power of a predetermined voltage to each parts of the electronic cassette 13 through a power source circuit 68. The battery 38 is small enough to be contained in the slim electronic cassette 13. The battery 38 can be taken out of the electronic cassette 13 and mounted on a specific cradle for recharging. The battery 38 may be recharged by a wireless power feeder.

In addition to the antenna 37, the electronic cassette 13 is provided with a socket 39. The socket 39, establishing wired communication with the console 14, is used when the wireless communication between the electronic cassette 13 and the console 14 is disabled due to a shortage of the battery 38 or the like. Connecting a cable of the console 14 to the socket 39 enables the wired communication with the console 14. At this time, the console 14 can feed power to the electronic cassette 13, if the power source circuit 68 has a recharging function.

The antenna 37 and the socket 39 are connected to a communication circuit 40. The communication circuit 40 mediates various types of information and signals including image data between the antenna 37 or the socket 39 and a control circuit 41, and between the antenna 37 or the socket 39 and a memory 42.

The FPD 35 has the imaging surface 36 that has a TFT active matrix substrate and a plurality of pixels 45 arranged on the TFT active matrix substrate. Each pixel 45 produces signal charge by an amount corresponding to the amount of the X-rays incident thereon. The plurality of pixels 45 are arranged into a two-dimensional matrix with n rows (extending X direction) and m columns (extending Y direction) at a predetermined pitch.

The FPD 35 is of an indirect conversion type, having a scintillator (phosphor) for converting the X-rays into visible light. The pixels 45 perform photoelectric conversion of the visible light produced by the scintillator. The scintillator is made of CsI (cesium iodide), GOS (gadolinium oxysulfide), or the like, and is opposed to the entire imaging surface 36 having the matrix of the pixels 45. The scintillator and the TFT active matrix substrate may adopt either a PSS (penetration side sampling) method or an ISS (irradiation side sampling) method. In the PSS method, the scintillator and the substrate are disposed in this order from an X-ray incident side. In the ISS method, the scintillator and the substrate are disposed in reverse order. Note that, a direct conversion type FPD, which has a conversion layer (amorphous selenium or the like) for directly converting the X-rays into electric charge, may be used instead.

The pixel (normal pixel) 45 is composed of a photodiode 46, a capacitor (not shown), and a thin film transistor (TFT) 47. The photodiode 46 being a photoelectric conversion element produces electric charge (electron and hole pairs) upon entry of the visible light. The capacitor accumulates the produced electric charge. The TFT 47 functions as a switching element.

The photodiode 46 is composed of a semiconducting layer (of a PIN type, for example) for producing the electric charge, and upper and lower electrodes disposed on the top and bottom of the semiconducting layer. The lower electrode of the photodiode 46 is connected to the TFT 47. The upper electrode of the photodiode 46 is connected to a bias line 48. The number of the bias lines 48 coincides with the number of rows (n rows) of the pixels 45 arranged in the imaging surface 36. All the n bias lines 48 are connected to a bias power source 50 through a bus 49. The bias power source 50 applies a bias voltage Vb to the upper electrode of every photodiode 46 through the bus 49 and the bias lines 48. Since the application of the bias voltage Vb produces an electric field in the semiconducting layer, the electric charge (electron and hole pairs) produced in the semiconducting layer by the photoelectric conversion is attracted to the upper and lower electrodes, one of which has positive polarity and the other has negative polarity. Thereby, the electric charge is accumulated in the capacitor.

A gate electrode of the TFT 47 is connected to a scan line 51. A source electrode of the TFT 47 is connected to a signal line 52. A drain electrode of the TFT 47 is connected to the photodiode 46. The scan lines 51 and the signal lines 52 are routed into a lattice. The number of the scan lines 51 coincides with the number of the rows (n rows) of the pixels 45 arranged in the imaging surface 36. The number of the signal lines 52 coincides with the number of the columns (m columns) of the pixels 45. Every scan line 51 is connected to a gate driver 53, and every signal line 52 is connected to a signal processing circuit 54.

The gate driver 53 drives the TFTs 47 to carry out the charge accumulation operation in which each pixel 45 accumulates the signal charge by an amount corresponding to the amount of the X-rays incident thereon, a readout operation (actual discharge operation) in which the signal charge is read out from the pixels 45, and the reset operation (idle discharge operation). The control circuit 41 controls start timing of each of the above operations carried out by the gate driver 53.

In the charge accumulation operation, every TFT 47 is turned off, so every pixel 45 accumulates the signal charge. In the readout operation, the gate driver 53 sequentially issues gate pulses G1 to Gn each of which drives the TFTs 47 of the same row at a time. Thereby, the scan lines 51 are activated one by one so as to turn on the TFTs 47 connected to the activated scan line 51 on a row-by-row basis. Upon turning on the TFT 47, the signal charge accumulated in the capacitor of the pixel 45 is read out to the signal line 52, and inputted to the signal processing circuit 54.

The signal processing circuit 54 includes integration amplifiers 60, a multiplexer (MUX) 61, an A/D converter (A/D) 62, and the like. The integration amplifier 60 is connected to each signal line 52 on a one-by-one basis. The integration amplifier 60 is composed of an operational amplifier 60a and a capacitor 60b connected between input and output terminals of the operational amplifier 60a. One of the input terminals of the operation amplifier 60a is connected to the signal line 52. The other input terminal of the operational amplifier 60a is connected to a ground (GND). A reset switch 60c is connected in parallel with the capacitor 60b. The integration amplifier 60 converts by integration the electric charge inputted from the signal line 52 into each of voltage signals D1 to Dm, and output each of the voltage signals D1 to Dm. The output terminal of every operational amplifier 60a is connected to the MUX 61 through another amplifier 63 and a sample holder (S/H) 64. An output of the MUX 61 is connected to the A/D 62.

The MUX 61 successively chooses one of the plurality of integration amplifiers 60 connected in parallel, and inputs the voltage signals D1 to Dm outputted from the chosen integration amplifiers 60 in series to the A/D 62. The A/D 62 converts the voltage signals D1 to Dm into digital data, and outputs the digital data to the memory 42 contained in the electronic cassette 13. Another amplifier may be provided between the MUX 61 and the A/D 62.

After the MUX 61 successively reads out from the integration amplifiers 60 the voltage signals D1 to Dm of one row, the control circuit 41 outputs a reset pulse RST to the integration amplifiers 60 to turn on the reset switches 60c. Thus, the signal charge of one row accumulated in the capacitors 60b is discharged and reset. Upon the reset of the integration amplifiers 60, the gate driver 53 outputs the gate pulse of the next row to start reading out the signal charge from the pixels 45 of the next row. By sequential repetition of this operation, the signal charge is read out from the pixels 45 of every row.

After completion of the readout from every row, the image data representing the X-ray image of one frame is stored in the memory 42. This image data is read out from the memory 42, and outputted to the console 14 through the communication circuit 40. Thereby, the electronic cassette 13 detects the X-ray image of the imaged portion.

Dark charge occurs in the semiconducting layer of the photodiode 46 irrespective of the presence or absence of entry of the X-rays. Due to the application of the bias voltage Vb, the dark charge is accumulated in the capacitor of the pixel 45. The dark charge occurring in the normal pixels 45 becomes noise of the image data, and therefore the reset operation is carried out to remove the dark charge. In other words, the reset operation is an operation in which the dark charge produced in the pixels 45 is discharged through the signal lines 52. The reset operation is performed periodically before starting the radiography. When the start of the radiography is commanded, the reset operation is performed forcefully, and then the preliminary imaging and the main imaging are carried out.

The reset operation adopts a sequential reset method, for example, by which the pixels 45 are reset on a row-by-row basis. In the sequential reset method, as with the readout operation of the signal charge, the gate driver 53 sequentially issues the gate pulses G1 to Gn to the signal lines 51 to turn on the TFTs 47 of the pixels 45 on a row-by-row basis. While the TFT 47 is turned on, the dark charge flows from the pixel 45 through the signal line 52 into the capacitor 60b of the integration amplifier 60. In the reset operation, in contrast to the readout operation, the MUX 61 does not read out the electric charge accumulated in the capacitors 60b. In synchronization with the issue of each of the gate pulses G1 to Gn, the control circuit 41 outputs the reset pulse RST. The reset pulse RST turns on the reset switches 60c, so the electric charge accumulated in the capacitors 60b is discharged, and the integration amplifiers 60 are reset.

Instead of the sequential reset method, a parallel reset method or all pixels reset method may be used. In the parallel reset method, a plurality of rows of pixels are grouped together, and sequential reset is carried out in each group, so as to concurrently discharge the dark charge from the rows of the number of the groups. In the all pixels reset method, the gate pulse is inputted to every row to discharge the dark charge from every pixel at a time. Adoption of the parallel reset method and the all pixel reset method allows speeding up the reset operation.

Upon receiving the inquiry signal from the controller 21 of the source controller 11, the control circuit 41 performs the reset operation of the FPD 35, and sends the emission permission signal back to the source controller 11. After that, upon receiving the emission start signal, the control circuit 41 shifts the FPD 35 from the reset operation to the charge accumulation operation.

The FPD 35 has, in the common imaging surface 36, not only the normal pixels 45 each connected to the signal line 52 through the TFT 47, but also a plurality of detection pixels 65 each of which is connected to the signal line 52 without through the TFT 47. The detection pixels 65 are used for detecting the X-ray dose applied to the imaging surface 36 through the imaged portion. The detection pixel 65 functions as an emission stop detection sensor and an AEC sensor. The number of the detection pixels 65 occupies about a few percent of a total pixel number of the imaging surface 36.

Figure 5A:
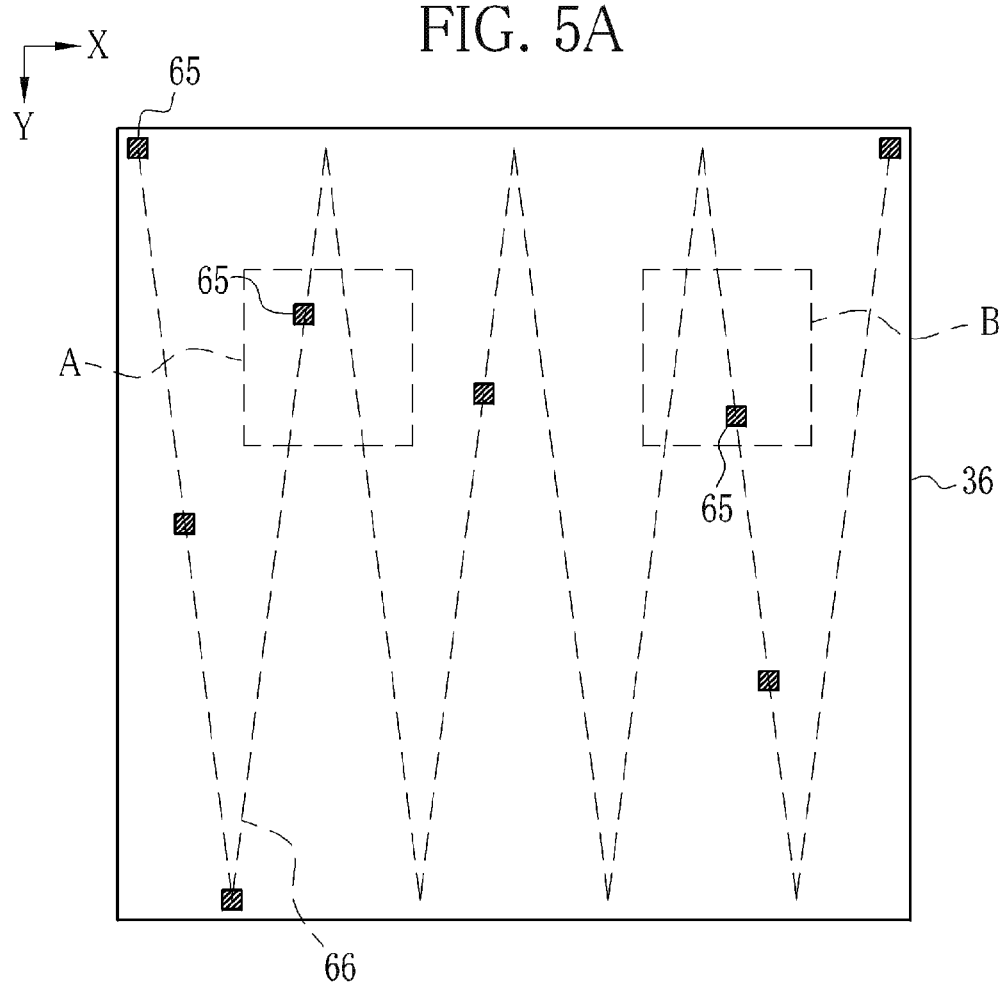
FIG. 5A is an explanatory view showing an example of the distribution of detection pixels in an FPD.
Figure 5B:
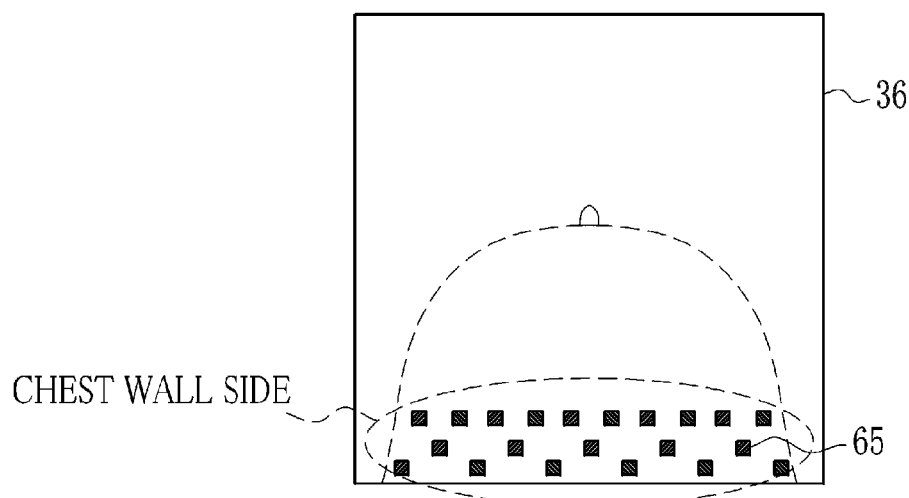
FIG. 5B is an explanatory view showing another example of the distribution of the detection pixels in the FPD.

As shown in FIG. 5A, the detection pixels 65 are disposed along a zigzag line 66 symmetric with respect to the center of the imaging surface 36 as shown by a broken line, so as to be uniformly distributed in the imaging surface 36 without being localized. For example, one detection pixel 65 is laid out every two to three signal lines 52, and two or more detection pixels 65 are not laid out in the single signal line 52. The positions of the detection pixels 65 are known in manufacturing the FPD 35, and the FPD 35 has a nonvolatile memory (not shown) that stores the position (coordinates) of every detection pixel 65 in advance. Note that, the disposition of the detection pixels 65 shown in FIG. 5A is just an example, and is appropriately changeable. In a mammography system for inspecting a breast, as shown in FIG. 5B, the detection pixels 65 are preferably localized on a chest wall side.

Since the detection pixel 65 is connected to the signal line 52 directly without through the TFT 47, the signal charge produced in the detection pixel 65 immediately flows into the signal line 52. For example, the detection pixel 65 continues outputting the signal charge, even if the normal pixels 45 disposed in the same row as that of the detection pixel 65 are in the middle of the charge accumulation operation. Thus, the electric charge produced in the detection pixel 65 always flows into the capacitor 60b of the integration amplifier 60 in the signal line 52 connected to the detection pixel 65. During the charge accumulation operation, the electric charge that is produced by the detection pixel 65 and accumulated in the capacitor 60b is outputted as a voltage value through the MUX 61 to the A/D 62 at predetermined sampling intervals.

In FIG. 4, the AEC circuit 67 driven by the control circuit 41 works only during the preliminary imaging. The AEC circuit 67 obtains through the A/D 62 the voltage values (hereinafter called AEC detection signals) from the signal lines 52 connected to the detection pixels 65.

Figures 6, 7:
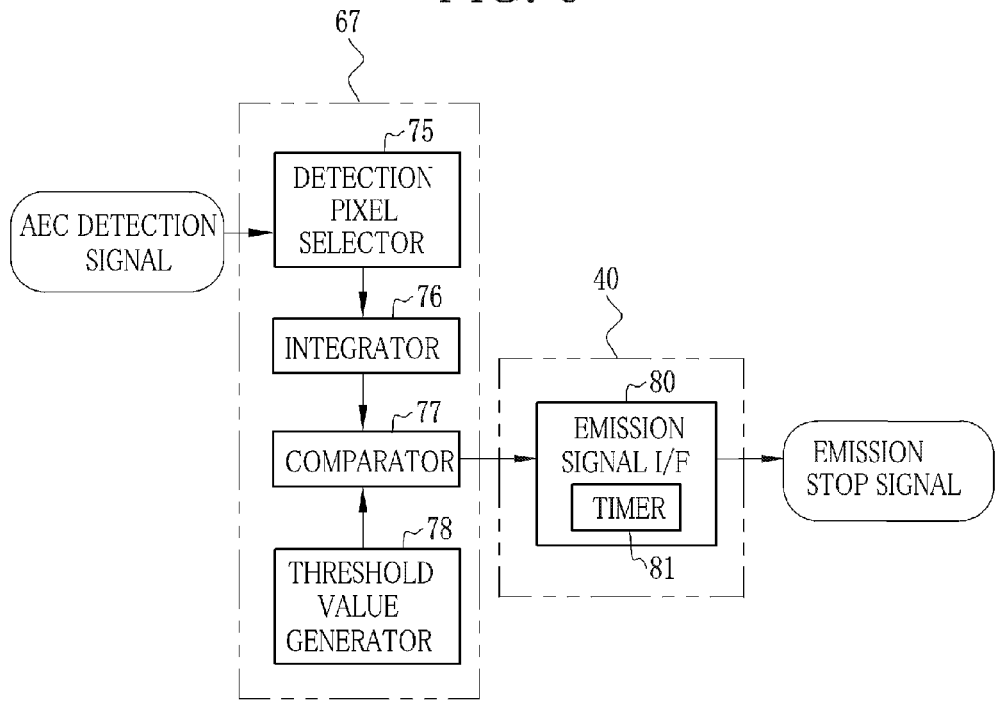
FIG. 6 is a block diagram of an AEC circuit and a communication circuit of the electronic cassette.
FIG. 7 is a table of exposure conditions set up in a console.

As shown in FIG. 6, the AEC circuit 67 includes a detection pixel selector 75, an integrator 76, a comparator 77, and a threshold value generator 78. The detection pixel selector 75 selects which detection pixels 65 to use in the AEC out of the plurality of detection pixels 65 distributed in the imaging surface 36, based on irradiation area data from the console 14. The integrator 76 integrates a mean value, a maximum value, a mode value, or a total value of the AEC detection signals from the detection pixels 65 selected by the detection pixel selector 75. The comparator 77 starts monitoring an integral value of the AEC detection signals from the integrator 76, when the start of X-ray emission is detected. The comparator 77 compares at predetermined intervals the integral value with an emission stop threshold value provided by the threshold value generator 78. If the integral value reaches the emission stop threshold value, the comparator 77 issues an emission stop signal.

Furthermore, the AEC circuit 67 is provided with an emission stop detection circuit that detects the stop of X-ray emission during the main imaging by comparing the AEC detection signals from the detection pixels 65 with a predetermined detection threshold value.

The communication circuit 40 is provided with an emission signal I/F 80 in addition to the antenna 37 and the socket 39 described above. To the emission signal I/F 80, the emission signal I/F 25 of the source controller 11 is connected. The emission signal I/F 80 performs reception of the inquiry signal, transmission of the emission permission signal in response to the inquiry signal, reception of the emission start signal, and output from the comparator 77 i.e. transmission of the emission stop signal and the like (only the transmission of the emission stop signal is illustrated in FIG. 6).

The emission signal I/F 80 has a timer 81. The timer 81 measures a preliminary irradiation time, that is, time between the reception of the emission start signal and the transmission of the emission stop signal by the emission signal I/F 80 during the preliminary imaging. A measurement result of the timer 81 is transmitted to the control circuit 41, and then is transmitted from the control circuit 41 to a cassette controller 98 (see FIG. 9) of the console 14 through the communication circuit 40. The integral value of the AEC detection signals calculated by the integrator 76 at the time of transmitting the emission stop signal is also transmitted to the cassette controller 98. The source controller 11 may measure the preliminary irradiation time, and transmit the measured preliminary irradiation time to the cassette controller 98 through the communication I/F 22 and the communication circuit 40.

The console 14 is communicatably connected to the electronic cassette 13 in a wired or wireless method, to control the operation of the electronic cassette 13. To be more specific, the console 14 transmits the exposure condition to the electronic cassette 13 to set up a signal processing condition (a gain of the amplifier for multiplying a voltage corresponding to the accumulated signal charge and the like) of the FPD 35. Also, the console 14 turns on and off the electronic cassette 13, and puts the electronic cassette 13 into a power saving mode, a standby mode, and the like.

The console 14 applies various types of image processing such as offset correction, gain correction, and defect correction to the X-ray image data transmitted from the electronic cassette 13. In the defect correction, a pixel value of the column having the detection pixel 65 is interpolated using a pixel value of the adjacent column without having the detection pixel 65. The X-ray image after subjected to the image processing is displayed on a monitor 89 (see FIG. 8) of the console 14, and its data is written to a storage device 87 and a memory 86 (see FIG. 8) of the console 14, or an image storage server connected to the console 14 through a network. The electronic cassette 13 may perform the above various types of image processing.

To the console 14, an examination order including information about the sex and age of the patient, the body portion to be imaged, an examination purpose, and the like is inputted from an input device 90 such as a keyboard. This examination order is displayed on the monitor 89. The examination order is inputted from an external system e.g. HIS (hospital information system) or RIS (radiography information system) that manages patient data and examination data related to radiography, or inputted manually by the radiological technician. The examination order includes the body portion to be imaged e.g. head, chest, abdomen, and the like, and an imaging direction e.g. anterior, medial, diagonal, PA (X-rays are applied from a posterior direction), and AP (X-rays are applied from an anterior direction). The radiological technician checks the contents of the examination order on the monitor 89, and inputs the exposure condition corresponding to the contents of the examination order through an operation screen of the console 14.

As shown in FIG. 7, one exposure condition is settable for each body portion in the console 14. The exposure condition includes the tube voltage, the tube current, the irradiation area for use in selecting the detection pixels 65, the emission stop threshold value for judging the stop of X-ray emission during the preliminary imaging by comparison with the integral value of the AEC detection signals, a necessary X-ray dose being an X-ray dose necessary for the radiography, and the like. This information about the exposure condition is stored in the storage device 87. The radiological technician manually sets the exposure condition of the source controller 11 with referring to the exposure condition of the console 14.

The irradiation area is the most noteworthy area in diagnosis that is specified in each body portion, and an area from which the AEC detection signal is stably obtainable. One or more detection pixels 65 present within the irradiation area are used in the AEC. Referring to FIG. 5A, in a case where the imaged body portion is the chest, for example, areas "A" and "B" that are enclosed by broken lines, i.e. areas of the lung fields are assigned as the irradiation areas. Each irradiation area is represented by X and Y coordinates. If the irradiation area is in a rectangular shape, as in the case of this embodiment, the X and Y coordinates of two points connected by a diagonal line are stored. The X and Y coordinates correspond to the positions of the pixels 45 in the imaging surface 36. The X and Y coordinates are Cartesian coordinates in which an X axis extends in a direction parallel to the scan lines 51, a Y axis extends in a direction parallel to the signal lines 52, and the most upper left pixel 45 is assigned as an origin point (0, 0).

If noise added to the AEC detection signals results in a low S/N ratio, the main exposure condition that is determined based on the low S/N ratio becomes less reliable. To secure the reliability, the preliminary irradiation time is preferably made long. On the other hand, the preliminary irradiation time has to be as short as possible in order to reduce radiation exposure to the patient. For this reason, the emission stop threshold value is set at a minimum integral value of the AEC detection signals, as long as the main exposure condition is reliably determined without the adverse effect of various types of noise added to the AEC detection signals.

The necessary X-ray dose corresponds to an integral value of the AEC detection signals the application of which allows obtainment of the X-ray image having desirable image quality adequate for diagnosis in the radiography.

Figure 8:
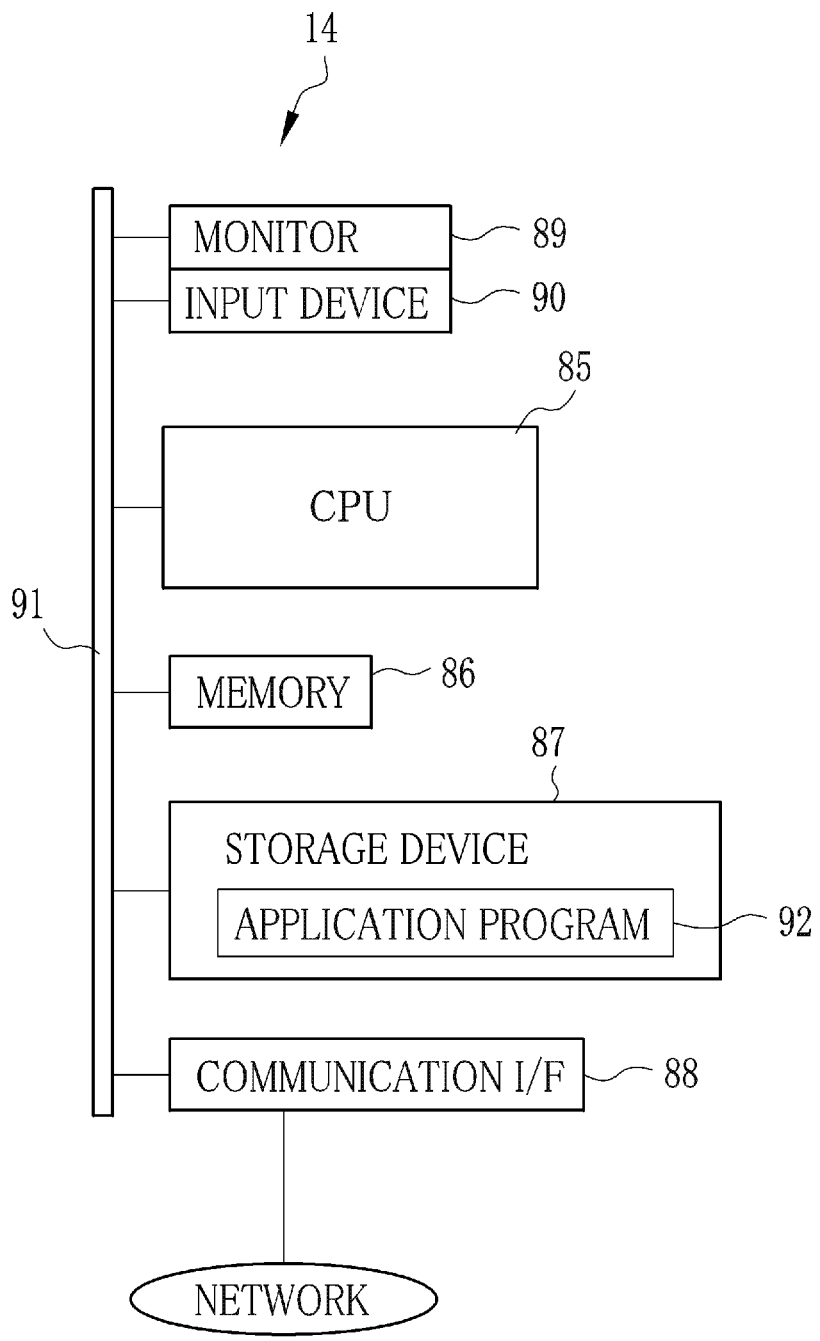
FIG. 8 is a block diagram of the console.

As shown in FIG. 8, the console 14 is composed of a computer having a CPU 85, the memory 86, the storage device 87, a communication I/F 88, the monitor 89, and the input device 90. These components are connected to each other via a data bus 91.

The storage device 87 is a hard disk drive (HDD), for example. The storage device 87 stores a control program and an application program 92. Running the application program 92 makes the console 14 perform various functions related to the radiography, such as display processing of the examination order and the X-ray image, image processing of the X-ray image, and a setup of the exposure condition.

The memory 86 is a work memory used when the CPU 85 executes. The CPU 85 loads the control program stored on the storage device 87 into the memory 86, and runs the programs for centralized control of the computer. The communication I/F 88 functions as a network interface for performing wireless or wired transmission control from/to an external device such as the RIS, the HIS, the image server, and the electronic cassette 13. The input device 90 includes a keyboard and a mouse, or a touch panel integrated with the monitor 89.

Figure 9:
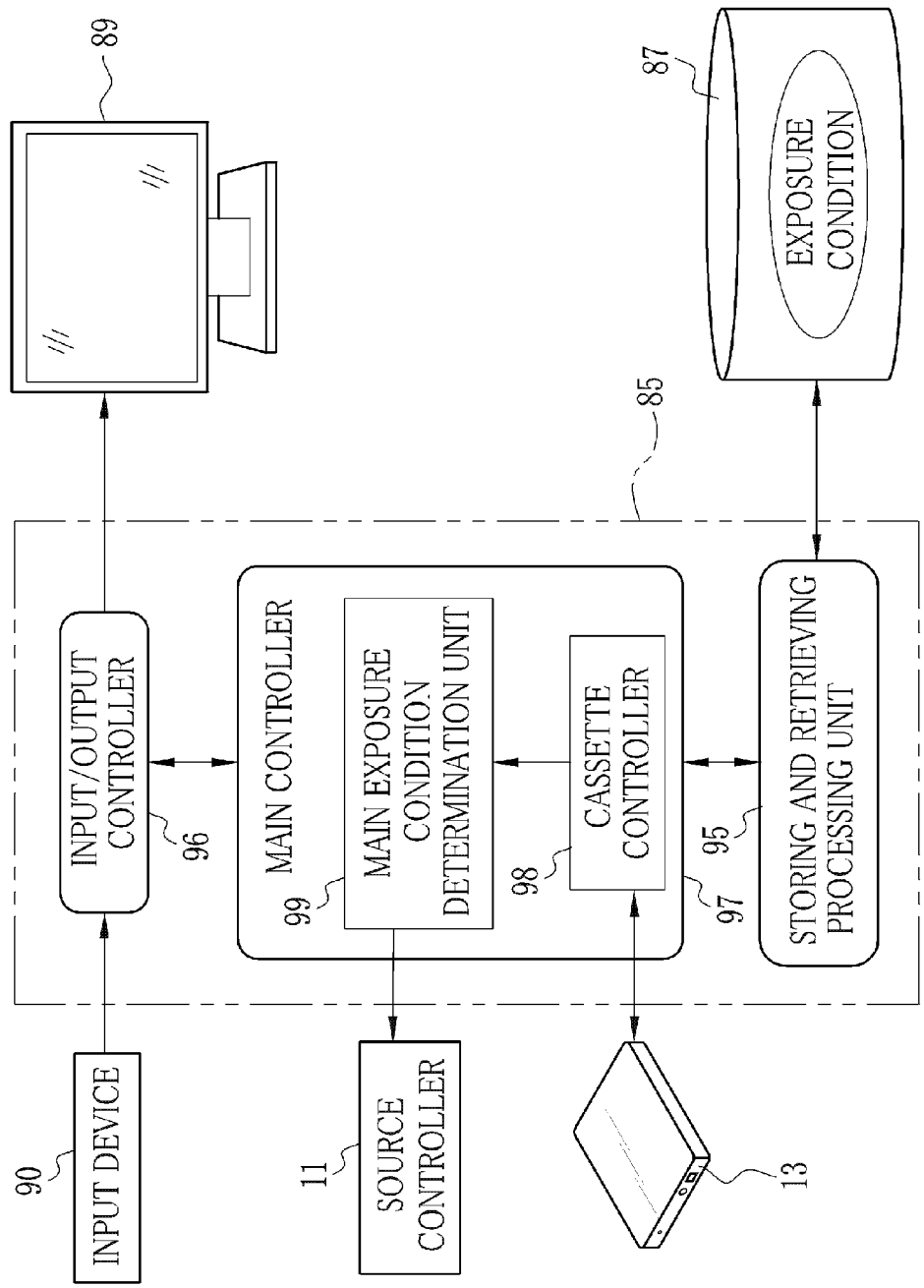
FIG. 9 is a block diagram showing the structure of a CPU and the connection between the CPU and other devices.

As shown in FIG. 9, by running the application program 92, the CPU 85 of the console 14 functions as a storing and retrieving processing unit 95, an input/output controller 96, and a main controller 97. The storing and retrieving processing unit 95 stores various types of data to the storage device 87, and retrieves the data from the storage device 87. The input/output controller 96 reads out drawing data from the storage device 87 in response to operation on the input device 90, and outputs to the monitor 89 various operation screens of GUIs based on the read drawing data. The input/output controller 96 receives input of operation commands from the input device 90 through the operation screens. The main controller 97, which includes a cassette controller 98 for controlling the operation of the electronic cassette 13 and a main exposure condition determination unit 99 for determining the main exposure condition, performs centralized control of the console 14. In addition to above, the CPU 85 works as an image processing unit for performing various types of image processing such as the offset correction, the gain correction, and the defect correction, and a communication unit for establishing communications with the source controller 11 and the electronic cassette 13. These functions may be embodied by hardware instead of software.

The cassette controller 98 receives information of the irradiation area and information of the emission stop threshold value, which are included in the chosen exposure condition, from the storing and retrieving processing unit 95, and provides the information to the electronic cassette 13.

The main exposure condition determination unit 99 receives information of the necessary X-ray dose, which is included in the chosen exposure condition, from the storing and retrieving processing unit 95. The main exposure condition determination unit 99 obtains from the cassette controller 98 the preliminary irradiation time measured by the timer 81 and the integral value of the AEC detection signals produced by the integrator 76 at the time of issuing the emission stop signal. The integral value of the AEC detection signals corresponds to an integral value of the received X-ray dose in the preliminary imaging.

The main exposure condition determination unit 99 determines an X-ray irradiation time in the main imaging (hereinafter called main irradiation time), being one item of the main exposure condition, based on the necessary X-ray dose, the preliminary irradiation time, and the integral value of the received X-ray dose in the preliminary imaging. To be more specific, the integral value of the received X-ray dose is divided by the preliminary irradiation time, to obtain a received X-ray dose (an instantaneous value of the received X-ray dose) per unit of time in the preliminary imaging. Then, the integral value of the received X-ray dose is subtracted from the necessary X-ray dose, because the preliminary imaging is effective as with the main imaging, and the X-ray dose corresponding to the integral value has already been applied to the imaged portion. Then, this subtraction result is divided by the received X-ray dose per unit of time, to obtain the main irradiation time. The main exposure condition determination unit 99 transmits information of the main irradiation time, which is determined as described above, to the source controller 11. In this occasion, the main irradiation time itself may be transmitted, or a division of the main irradiation time by the preliminary irradiation time (a ratio of the main irradiation time to the preliminary irradiation time) may be transmitted.

As another item of the main exposure condition, a current-time product (main current-time product) may be determined instead of the main irradiation time. In this case, as in the case of determining the main irradiation time, the integral value of the AEC detection signals i.e. the integral value of the received X-ray dose is divided by a current-time product in the preliminary imaging, to obtain a received X-ray dose per unit of a current-time product i.e. an instantaneous value of the received X-ray dose in the preliminary imaging. Then, the integral value of the received X-ray dose is subtracted from the necessary X-ray dose, and this subtraction result is divided by the instantaneous value of the received X-ray dose to obtain the main current-time product. Information of the determined main current-time product is transmitted to the source controller 11. In this occasion, the main current-time product itself or a ratio of the main current-time product to the preliminary current-time product may be transmitted.

Figure 10:
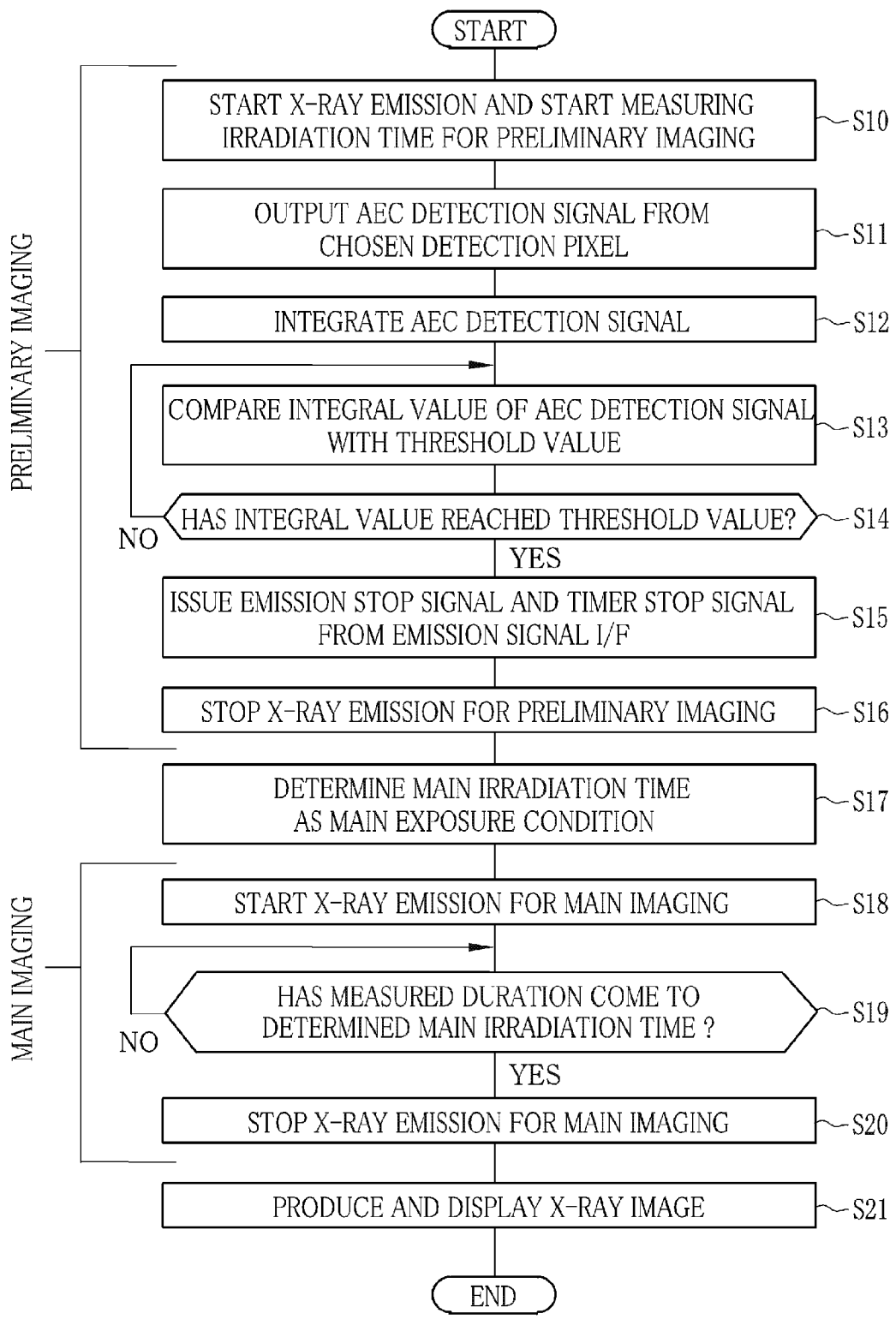
FIG. 10 is a flowchart of an X-ray imaging process.

Next, the operation of the X-ray imaging system 2 will be described with referring to a flowchart of FIG. 10.

The radiological technician makes the patient stand up at a predetermined position in front of the imaging stand 15 or lie down on the imaging table 16, depending on a condition of the patient and the body portion to be imaged. The height and the horizontal position of the electronic cassette 13, which is mounted on the imaging stand 15 or the imaging table 16 being used, are adjusted with respect to the position of the body portion to be imaged. In accordance with the position of the electronic cassette 13 and the size of the body portion, the height and the horizontal position of the X-ray source 10 and the size of the irradiation field are adjusted. After that, the electronic cassette 13 is turned on, and the exposure condition is inputted from the input device 90. The exposure condition, including the irradiation area and the emission stop threshold value, is transmitted to the electronic cassette 13 through the cassette controller 98. In a like manner, the exposure condition is set up in the source controller 11.

After a preparation for radiography is completed, the radiological technician half presses the emission switch 12. Thus, the warm-up start signal is transmitted to the source controller 11 to start warming up the X-ray source 10. After a lapse of predetermined time, the emission switch 12 is fully pressed, so the emission start signal is transmitted to the source controller 11 to start the X-ray emission in the preliminary imaging (S10).

The FPD 35 of the electronic cassette 13 periodically performs the reset operation until immediately before the start of X-ray emission. Upon receiving the emission start signal from the source controller 11, the FPD 35 halts the reset operation and shifts to the charge accumulation operation. In the charge accumulation operation, the X-rays that are incident during the preliminary imaging are converted into the electric charge, and the electric charge is accumulated.

In the electronic cassette 13, simultaneously with the charge accumulation operation of the FPD 35, the AEC circuit 67 performs the AEC based on the output of the detection pixels 65. The detection pixel selector 75 selects one or more AEC detection signals from one or more detection pixels 65 that are present within the irradiation area, out of the AEC detection signals from all the detection pixels 65 inputted from the A/D 62. The selected AEC detection signals are inputted to the integrator 76 (S11). The integrator 76 integrates the selected AEC detection signals (S12).

The threshold value generator 78 produces the emission stop threshold value provided by the cassette controller 98, and outputs the emission stop threshold value to the comparator 77. The comparator 77 compares the integral value of the AEC detection signals from the integrator 76 with the emission stop threshold value from the threshold value generator 78 (S13). If the integral value has reached the threshold value (YES in S14), the comparator 77 issues the emission stop signal. The emission stop signal from the comparator 77 is transmitted to the emission signal I/F 25 of the source controller 11 through the emission signal I/F 80 (S15).

When the emission signal I/F 25 receives the emission stop signal, the controller 21 of the source controller 11 stops supplying the electric power from the high voltage generator 20 to the X-ray source 10, and hence the X-ray emission is stopped in the preliminary imaging (S16). The FPD 35 continues the charge accumulation operation.

The timer 81 measures the preliminary irradiation time (S10 and S15). The measurement result of the timer 81 and the integral value of the AEC detection signals by the integrator 76 are transmitted to the cassette controller 98.

The main exposure condition determination unit 99 determines the main irradiation time based on the necessary X-ray dose received from the storing and retrieving processing unit 95 and the preliminary irradiation time and the integral value of the AEC detection signals received from the cassette controller 98 (S17). The determined main irradiation time is transmitted to the source controller 11.

The source controller 11 sets the timer 26 at a value of the main irradiation time determined by the main exposure condition determination unit 99, and automatically starts the X-ray emission for the main imaging without waiting for the operation on the emission switch 12 (S18). The moment when the measured duration has come to the set value (YES in S19), the X-ray emission is stopped (S20).

The FPD 35 continues the charge accumulation operation ever since the start of the preliminary imaging. Thus, the electric charge produced over the preliminary imaging and the main imaging is accumulated in each pixel 45. When the AEC circuit 67 detects the stop of X-ray emission in the main imaging at its emission stop detection circuit, the FPD 35 is shifted from the charge accumulation operation to the readout operation. The electric charge is read out from every pixel 45, and outputted as the time-series image data after the A/D conversion. After the readout operation, the FPD 35 performs the reset operation.

The image data outputted from the FPD 35 is transmitted to the console 14 through the communication circuit 40. The console 14 applies various types of image processing to the image data, and displays the image data on the monitor 89 as the X-ray image through the input/output controller 96 (S21).

In the above embodiment, the preliminary imaging is carried out in order to determine the main exposure condition. The main irradiation time, being an item of the main exposure condition, is determined based on the integral value of the AEC detection signals detected by the detection pixels 65 during the preliminary imaging, the preliminary irradiation time measured by the timer 81, and the necessary X-ray dose. Therefore, the main imaging is always carried out with an appropriate exposure condition, irrespective of individual difference in physique of the patient, the density of the internal body tissue, and the like.

Also, it becomes possible to save time and effort for the radiological technician to set up the exposure condition for each individual patient in the preliminary imaging. The main exposure condition is determined quickly with simple calculation, without the inconvenience of analyzing the X-ray image obtained during the preliminary imaging and detecting the body thickness. Therefore, time necessary for the radiography is shortened than ever before.

Since the AEC is carried out only during the preliminary imaging, no problem about delay in the emission stop signal occurs in the main imaging. This prevents deterioration in the image quality of the X-ray image and unnecessary radiation exposure to the patient.

No readout operation is carried out in the preliminary imaging, and the charge accumulation operation is continued from the start of the preliminary imaging to the end of the main imaging. The main exposure condition is determined only based on the AEC detection signals of the detection pixels 65 without output of the X-ray image, so the X-ray dose applied during the preliminary imaging is effectively used for production of the X-ray image. As a result, a radiation dose applied to the patient is reduced than ever before.

The reset operation may be performed upon the stop of X-ray emission in the preliminary imaging. The electric charge accumulated during the preliminary imaging is abandoned, and the charge accumulation operation may be restarted at the time of starting the X-ray emission in the main imaging. In this case, the integral value of the AEC detection signals is not subtracted from the necessary X-ray dose, and the necessary X-ray dose is divided by the integral value of the AEC detection signals per unit of time to obtain the main irradiation time.

Figure 11:
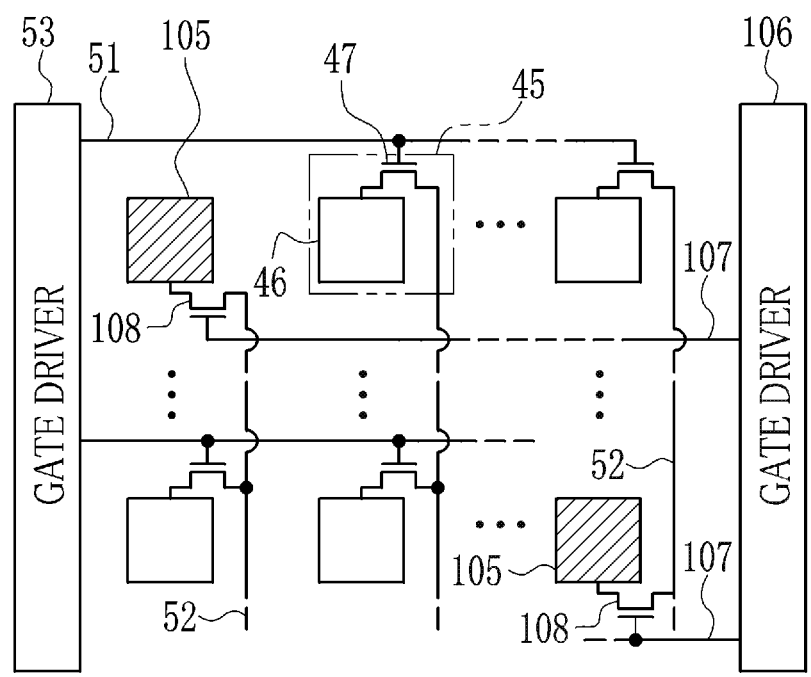
FIG. 11 is a block diagram showing detection pixels of another embodiment.

In the above embodiment, the detection pixel 65 that is directly connected to the signal line 52 without through the TFT 47 is used as the AEC sensor. However, as shown in FIG. 11, detection pixels 105 each having a TFT 108 that is driven by a gate driver 106 and a scan line 107 different from those of the normal pixels 45 may be used to read out the AEC detection signals independently from the signals from the normal pixels 45. In another case, with taking advantage of the fact that electric current flowing through the bias line 48 is in proportional to the amount of the electric charge produced in the normal pixel 45, the electric current flowing through the bias line 48 connected to the specific normal pixel 45 may be monitored to detect the received X-ray dose. In further another case, the received X-ray dose may be detected based on leak charge from the normal pixel 45 in a state where all the TFTs 47 are turned off. Furthermore, another AEC detection pixel that has structure different from that of the normal pixel 45 and is outputted independently of the normal pixel 45 may be provided coplanarly to the imaging surface 36.

In a case where the detection pixel 65 of the electronic cassette 13 fails or the communication between the source controller 11 and the electronic cassette 13 fails due to a break in a wire or the like, the emission stop signal could not be transmitted appropriately and the AEC could not work. Especially, the preliminary irradiation time set in the source controller 11 takes its maximum value, so the malfunction of the AEC causes an excessive radiation dose to the patient. For this reason, the electronic cassette 13 has a test mode in which test radiography is performed with every exposure condition prepared in the console 14 immediately after installation of the electronic cassette 13 or at the start of a day. Furthermore, the detection pixels 65 continue detecting the X-rays, even after the electronic cassette 13 transmits the emission stop signal to the source controller 11. If the stop of X-ray emission is detected within predetermined time, it is judged that the AEC is performed normally. If not, it is judged that any failure occurs, and a warning message is displayed on the monitor 89.

The console 14 and the electronic cassette 13 are separate in the above embodiment, but the console 14 may not be necessarily independent of the electronic cassette 13. The electronic cassette 13 may have the function of the console 14. For example, the electronic cassette 13 may have the functions of the cassette controller 98 and the main exposure condition determination unit 99, and the electronic cassette 13 may determine the main irradiation time. Likewise, the source controller 11 and the console 14 may be integrated into one unit. Conversely, a specific imaging control device having the functions of the cassette controller 98 and the like may be provided between the electronic cassette and the console, and the console may be charged with only simple operations, including the input of the exposure condition and the display of the X-ray image. The present invention may be applied to a mounted type X-ray image detecting device, instead of the electronic cassette being the portable X-ray image detecting device.

The present invention is applicable to a radiation imaging system using another type of radiation such as γ-rays instead of the X-rays.

Although the present invention has been fully described by the way of the preferred embodiment thereof with reference to the accompanying drawings, various changes and modifications will be apparent to those having skill in this field. Therefore, unless otherwise these changes and modifications depart from the scope of the present invention, they should be construed as included therein.

What is claimed is:

1. A radiation imaging apparatus that performs main imaging for taking a radiographic image for use in diagnosis and preliminary imaging prior to said main imaging for determining a main exposure condition being an exposure condition used in said main imaging, said radiation imaging apparatus comprising:
    a radiation image detecting device having a detection panel having an arrangement of a plurality of pixels each for receiving radiation emitted from a radiation source and passed through an imaged portion;
    a dose detection sensor for detecting a received radiation dose passed through said imaged portion;
    an automatic exposure controller for comparing an integral value of said received radiation dose with a predetermined threshold value, and automatically stopping emission of said radiation from said radiation source in said preliminary imaging if said integral value has reached said threshold value; and
    a main exposure condition determination unit for determining said main exposure condition based on said integral value of said received radiation dose detected during said preliminary imaging and a necessary radiation dose required for ensuring image quality of said radiographic image, said main exposure condition including a main irradiation time being an irradiation time with said radiation during said main imaging or a main time-current product being a time-current product used during said main imaging, said main imaging being carried out with use of said determined main exposure condition.

2. The radiation imaging apparatus according to claim 1, wherein said dose detection sensor is provided in said detection panel.

3. The radiation imaging apparatus according to claim 2, further comprising:
    a timer for measuring a preliminary irradiation time being said irradiation time with said radiation during said preliminary imaging, wherein
    said main exposure condition determination unit determines said main exposure condition in consideration of said preliminary irradiation time measured by said timer, in addition to said integral value of said received radiation dose and said necessary radiation dose.

4. The radiation imaging apparatus according to claim 3, wherein
    said main exposure condition determination unit divides said integral value of said received radiation dose during said preliminary imaging by said preliminary irradiation time or said current-time product during said preliminary imaging to calculate said received radiation dose per unit of time or per unit of said current-time product;
    said integral value of said received radiation dose is subtracted from said necessary radiation dose, and a subtraction result is divided by said received radiation dose per unit of time or per unit of said current-time product to calculate said main irradiation time or said main time-current product as said main exposure condition.

5. The radiation imaging apparatus according to claim 3, wherein
    said radiation image detecting device is shifted to said main imaging without discharging electric charge that is produced and accumulated in said pixels during said preliminary imaging; and
    after completion of said main imaging, said radiographic image is produced from said electric charge accumulated in said pixels over said preliminary imaging and said main imaging.

6. The radiation imaging apparatus according to claim 3, wherein a plurality of said dose detection sensors are uniformly distributed in an imaging surface of said detection panel.

7. The radiation imaging apparatus according to claim 6, further comprising:
    a detection sensor selector for selecting at least one of said dose detection sensors in accordance with said imaged portion, wherein
    automatic exposure control and determination of said main exposure condition are performed with use of a detection result from said selected dose detection sensor.

8. The radiation imaging apparatus according to claim 3, wherein a plurality of said dose detection sensors are locally distributed in an imaging surface of said detection panel.

9. The radiation imaging apparatus according to claim 8, further comprising:
    a detection sensor selector for selecting at least one of said dose detection sensors in accordance with said imaged portion, wherein
    automatic exposure control and determination of said main exposure condition are performed with use of a detection result from said selected dose detection sensor.

10. The radiation imaging apparatus according to claim 3, wherein said plurality of pixels include:
    a normal pixel for producing and accumulating signal charge in accordance with a radiation dose received in said normal pixel, and outputting said signal charge through a switching element to a signal line; and
    a detection pixel connected directly to said signal line, said detection pixel functioning as said dose detection sensor.

11. The radiation imaging apparatus according to claim 3, wherein said plurality of pixels include:
    a normal pixel for producing and accumulating signal charge in accordance with a radiation dose received in said normal pixel, and outputting said signal charge through a switching element to a signal line; and
    a detection pixel having another switching element driven independently of said switching element of said normal pixel, said detection pixel functioning as said dose detection sensor.

12. The radiation imaging apparatus according to claim 3, wherein said radiation image detecting device is an electronic cassette having said detection panel contained in a portable housing.

13. A control method of a radiation imaging apparatus that performs main imaging for taking a radiographic image for use in diagnosis and preliminary imaging prior to said main imaging for determining a main exposure condition being an exposure condition used in said main imaging, said control method comprising the steps of:
- emitting radiation from a radiation source to an imaged portion in said preliminary imaging;
- detecting a radiation dose received in a radiation image detecting device through said imaged portion;
- comparing an integral value of said received radiation dose with a predetermined threshold value;
- automatically stopping emission of said radiation from said radiation source and completing said preliminary imaging, if said integral value has reached said threshold value;
- determining said main exposure condition based on said integral value of said received radiation dose detected during said preliminary imaging and a necessary radiation dose required for ensuring image quality of said radiographic image, said main exposure condition including a main irradiation time being an irradiation time with said radiation during said main imaging or a main time-current product being a time-current product used during said main imaging; and
- carrying out said main imaging with use of said determined main exposure condition.

14. The control method according to claim 13, further comprising the steps of:
- measuring a preliminary irradiation time being said irradiation time with said radiation during said preliminary imaging, wherein
- in said step of determining said main exposure condition, said main exposure condition is determined in consideration of said preliminary irradiation time, in addition to said integral value of said received radiation dose and said necessary radiation dose.

15. A radiation imaging system that performs main imaging for taking a radiographic image for use in diagnosis and preliminary imaging prior to said main imaging for determining a main exposure condition being an exposure condition used in said main imaging, said radiation imaging system comprising:
- a radiation generating apparatus for emitting radiation to an imaged portion;
- a radiation image detecting device having a detection panel having an arrangement of a plurality of pixels each for receiving said radiation passed through said imaged portion;
- a dose detection sensor for detecting a received radiation dose passed through said imaged portion;
- a timer for measuring a preliminary irradiation time being an irradiation time with said radiation during said preliminary imaging;
- an automatic exposure controller for comparing an integral value of said received radiation dose with a predetermined threshold value, and automatically stopping emission of said radiation from said radiation generating apparatus in said preliminary imaging if said integral value has reached said threshold value; and
- a main exposure condition determination unit for determining said main exposure condition based on said integral value of said received radiation dose detected during said preliminary imaging, said preliminary irradiation time, and a necessary radiation dose required for ensuring image quality of said radiographic image, said main exposure condition including a main irradiation time being said irradiation time with said radiation during said main imaging or a main time-current product being a time-current product used during said main imaging, said main imaging being carried out with use of said determined main exposure condition.

* * * * *